United States Patent [19]

Nokihara

[11] Patent Number: 5,460,786
[45] Date of Patent: Oct. 24, 1995

[54] CLEAVAGE APPARATUS

[75] Inventor: Kiyoshi Nokihara, Kyoto, Japan

[73] Assignee: Shimadzu Corporation, Kyoto, Japan

[21] Appl. No.: 193,393

[22] Filed: Feb. 7, 1994

[30] Foreign Application Priority Data

Feb. 26, 1993 [JP] Japan .................................. 5-063337

[51] Int. Cl.⁶ .......................... G05B 17/00; C08F 2/00; C12M 1/40; G01N 33/00
[52] U.S. Cl. .......................... 422/116; 422/131; 422/134; 422/138; 436/89; 935/88
[58] Field of Search .................................. 422/116, 131, 422/134, 138; 935/88; 435/287; 436/89

[56] References Cited

U.S. PATENT DOCUMENTS

| | | | |
|---|---|---|---|
| 4,517,338 | 5/1985 | Urdea et al. | 525/54.11 |
| 4,746,490 | 5/1988 | Saneii | 422/62 |
| 5,039,488 | 8/1991 | Kohr | 422/68.1 |
| 5,106,585 | 4/1992 | Minami et al. | 422/68.1 |
| 5,223,435 | 6/1993 | Kohr | 436/89 |
| 5,288,464 | 2/1994 | Nokihara | 422/101 |

Primary Examiner—Robert J. Warden
Assistant Examiner—Christopher Y. Kim
Attorney, Agent, or Firm—Birch, Stewart, Kolasch & Birch

[57] ABSTRACT

A cleavage apparatus for obtaining a free peptide after assembly of a peptide on a solid support by solid-phase peptide synthesis equipped with a cleavage cocktail transport line installed between the column for cleavage containing a peptidyl resin and a cleavage cocktail supply bottle, through which a cleavage cocktail is supplied from the bottle to the column and recovered into the cleavage cocktail supply bottle from the column. This apparatus can provide easy, safe, rapid and reliable cleavage in a large scale peptide synthesis.

17 Claims, 2 Drawing Sheets

Conditions:
    Column: YMC ODS C18 (4.6 × 150 mm)
    Eluent: 0.01N HCl/CH$_3$CN=85/15→55/45 (30min)
    Flow rate: 1.0 ml/min
    Absorbance (UV): 210 nm

CLEAVAGE APPARATUS

BACKGROUND OF THE INVENTION

1. Field of the Invention

The present invention relates to a cleavage apparatus used for liberating a peptide assembled on a solid support by a solid-phase peptide synthesis.

2. Discussion of the Related Art

Generally, synthesis of DNA, RNA and peptides (hereinafter simply referred to as peptide synthesis) has been achieved by repeating a series of treatments of washing, coupling, washing and deprotection on a solid-support of glass beads or resin powder in a filter-attached reaction vessel. Also, in order to obtain a free peptide, a cleavage procedure is necessary after the above-mentioned treatments.

The chemical synthesis of a peptide requires extensive knowledge and sophisticated techniques, and amino acid derivatives for peptide synthesis are expensive. Therefore, the resulting peptide is referred to as a highly value-added substance. Reagents and therapeutics or diagnostic agents containing chemically synthesized peptides have sometimes brought a vast amount of profit. When such synthesized peptide is used for practical purposes, a relatively large amount is needed, i.e., at least 10 to 20 mg is necessary for use in research and more than 100 g for commercial use, pre-clinical tests or clinical use. A large scale or at least semi-large scale synthesis is thus indispensable for practical purposes.

However, in such a larger scale peptide synthesis using a conventional method (Boc-chemistry), a special reactor or cautious operation is needed because extremely dangerous reagents such as hydrogen fluoride or trifluoromethane-sulfonic acid (TFMSA) are used in large quantities at the final step of the cleavage procedure. In recent years, Fmoc-chemistry of solid-phase peptide synthesis has widely been used in the field of peptide chemistry, which permits cleavage treatment under less dangerous conditions. In the Fmoc-polyamide method, cleavage is done using TFA (trifluoroacetic acid). TFA is not a totally safe reagent and necessitates careful handling. The danger of TFA used in large quantities is still an actual concern in the field of art. Therefore, the development of a cleavage apparatus which permits easy, safe, rapid and reliable cleavage in a large scale peptide synthesis has long been sought.

SUMMARY OF THE INVENTION

The object of the present invention is to provide a cleavage apparatus which permits easy, safe, rapid and reliable cleavage in a large scale peptide synthesis.

The inventor of the present invention has conducted intensive studies to achieve the above object, and has found it useful to perform cleavage by circulating a cleavage cocktail in a closed system. After further developmental work, the inventor has completed the present invention.

In summary, the present invention relates to a cleavage apparatus, which is characterized by having a cleavage cocktail transport line connecting between a peptide synthesis column containing a peptide or a side chain protected peptide bound to the solid support after the completion of peptide assembly (hereinafter simply referred to as a peptidyl resin) and a cleavage cocktail supply bottle, through which the cleavage cocktail is supplied from the cleavage cocktail supply bottle to the peptide synthesis column and recovered from the peptide synthesis column into the cleavage cocktail supply bottle.

In the present invention, a cleavage apparatus is defined as an apparatus for cleaving the peptide-resin (solid support) bond and simultaneously removing the side chain protecting groups to liberate a desired peptide assembled on the solid support by a solid-phase peptide synthesis, and is exemplified by the apparatus shown in FIG. 1.

The cleavage apparatus has a cleavage cocktail transport line connecting between a peptide synthesis column containing a peptidyl resin and a cleavage cocktail supply bottle, through which the cleavage cocktail is supplied from the bottle to the column and recovered into the bottle therefrom. By changing the direction of the flow of the cleavage cocktail in the cleavage cocktail transport line, the cleavage cocktail is stirred and transported, and by repeating the cycle of stirring and transportation, the cleavage cocktail is circulated. After circulated for a given period of time, the cleavage cocktail is recovered into the cleavage cocktail supply bottle through the cleavage cocktail transport line. The thus-recovered cleavage cocktail in the cleavage cocktail supply bottle contains the desired peptide dissolved therein, which has been cleaved from the resin and whose side chain have protecting groups been removed.

The cleavage cocktail used in the present invention is a mixture of one or more reagents suitable for liberating the desired peptide, selected from the reagents used for cleavage in an ordinary solid-phase peptide synthesis, such as TFA, anisole, thioanisole, ethanedithiol, dimethyl sulfide (DMS), ethyl methyl sulfide (EMS), phenol and thiophenol, and is not subject to limitation.

By the use of the cleavage apparatus of the present invention, a large amount of peptide can be treated in an easy, safe, rapid and reliable manner.

BRIEF DESCRIPTION OF THE DRAWINGS

The present invention will become more fully understood from the detailed description given hereinbelow and the accompanying drawings which are given by way of illustration only and thus, are not limitative of the present invention, and wherein.

Figure 1:
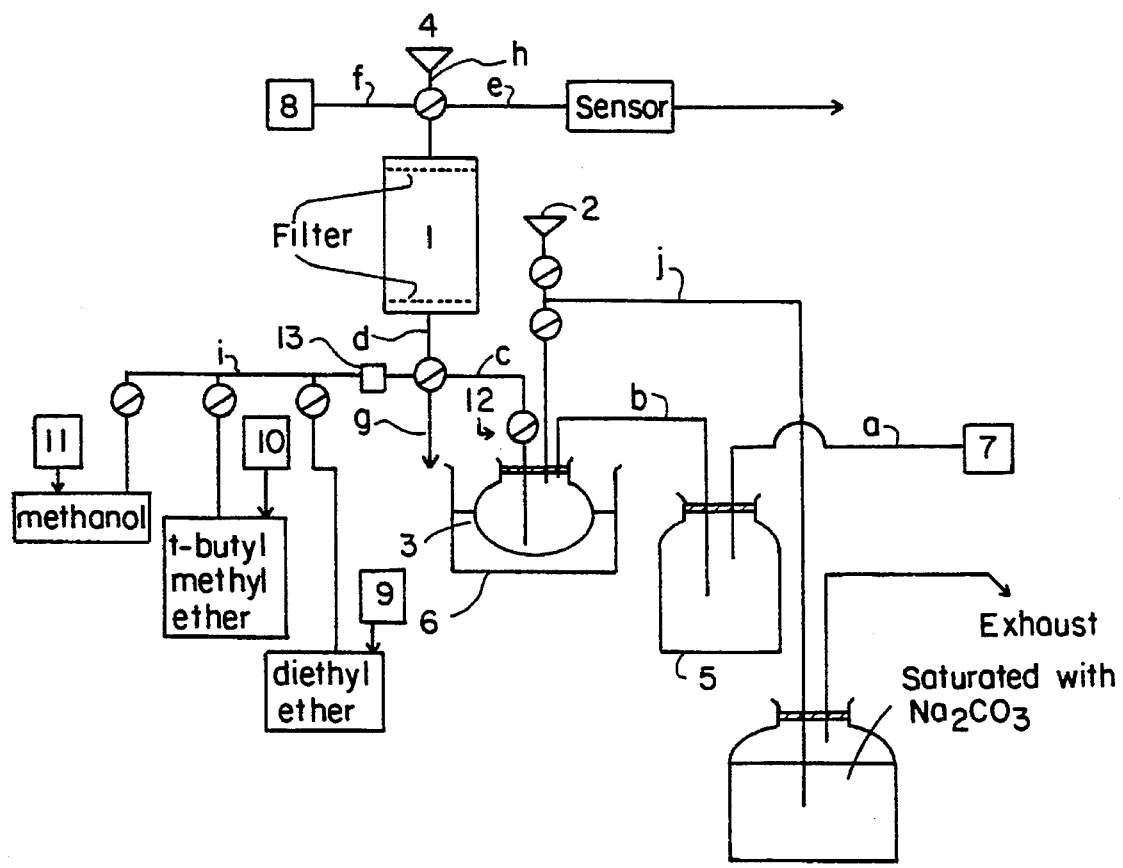
FIG. 1 is a schematic illustration of the cleavage apparatus of the present invention.

The reference numerals in FIG. 1 denote the following elements: Element 1 is a synthesis reaction column packed with resin; element 2, a funnel; element 3, a flask; element 4, a funnel; element 5, a container; element 6, an outside bath; elements 7 to 11, nitrogen gas; element 12, a valve; element 13, a pump; and elements a to j, lines.

DETAILED DESCRIPTION OF THE INVENTION

The cleavage procedure in the present invention for liberating the desired peptide from the solid support (resin) after the completion of peptide assembly is described in detail. The cleavage apparatus shown in FIG. 1 is used as a typical embodiment of the present invention.

Step (1): After solid-phase peptide synthesis in a continuous flow method, i.e., acylation (coupling) and subsequent removal of the Nα-protecting group, is complete, the column used for the synthesis, as such, is attached to the cleavage apparatus shown in FIG. 1 as a synthesis reaction column 1. When a solid-phase peptide synthesis is conducted in a batch-wise manner, the resulting peptidyl resin is packed in the reaction column 1.

Step (2): As washing liquids, methanol, t-butyl methyl ether and diethyl ether, in this order, are supplied to the synthesis reaction column 1 through line i to wash the peptidyl resin obtained. Alternatively, each washing liquid may be supplied from a funnel 2 to a flask 3 and further to the synthesis reaction column 1 to wash the peptidyl resin. After washing, the resulting waste liquid is discharged through line e. By supplying nitrogen gas 8 under increased pressure to the synthesis reaction column 1 through the line f, purging the synthesis reaction column 1 and discharging the gas through line g, the peptidyl resin in the synthesis reaction column 1 is dried. It is also possible to dry the peptidyl resin by supplying nitrogen gas 7, in place of nitrogen gas 8, under increased pressure to the synthesis reaction column 1 through lines a, b, c and d, purging the synthesis reaction column 1 and discharging the gas through line e. However, when peptide synthesis is conducted in a batch-wise manner and the dry resin can be packed in the reaction column 1, this operation may be omitted.

Step (3): By supplying nitrogen gas 8 under increased pressure to the synthesis reaction column 1 through line f and discharging it through line g, the inside of synthesis reaction column 1 is dried.

Step (4): The cleavage cocktail is supplied from the funnel 2 to the flask 3 (preferably eggplant-type flask). The cleavage cocktail in the flask 3 enters the synthesis reaction column 1 through lines c and d. The lines c and d function as cleavage cocktail transport lines in the cleavage apparatus.

It is necessary to control the temperature in the flask 3 in some cases, depending on the type of the peptide which is subject to cleavage and the type of side chain protecting groups. In this case, cooling or heating is added as necessary using an outside bath 6 whose temperature can be controlled by a microprocessor. For example, when amino acids constituting the peptide are acid-labile, it is preferable to cool the cleavage cocktail to about 4° C. before its injection into the synthesis reaction column 1 to prevent side reactions. Although it is sometimes preferable to change the temperature over time, for example, at the initial and intermediate stages of reaction, all these conditions depend on the type of the peptide which is subject to cleavage and the type of side chain protecting groups, and preferable conditions for each case are known to those skilled in the art. Usually, a cooled cleavage cocktail is commonly used at the initial stage.

Step (5): Nitrogen gas 8 is supplied under increased pressure to the synthesis reaction column 1 through the line f, to return the cleavage cocktail, which has entered the synthesis reaction column 1 in Step (4), to the flask 3 through the above-described cleavage cocktail transport lines (i.e., lines d and c).

Step (6): The cleavage cocktail in the flask 3 is again injected into the synthesis reaction column 1 through the cleavage cocktail transport lines (i.e., lines c and d).

Step (7): The above-described Steps (5) and (6) are repeated in about 9 to 18 cycles (for about 90 minutes at intervals of about 5 to 10 minutes) to complete cleavage for the desired peptide. It is necessary, however, to take longer intervals than usual, i.e., for about 5 to 8 hours at intervals of about 20 to 30 minutes, when the desired peptide contains Arg(Mtr) or Arg(Pmc) residues.

Step (8): After completion of cleavage, nitrogen gas 8 is supplied under increased pressure through the line f as necessary to completely return the cleavage cocktail to the flask 3. Co-washing is performed. Specifically, after a small amount of TFA or acetic acid for washing is supplied from the funnel 4 to the synthesis reaction column 1 through the line h, nitrogen gas 8 is supplied under increased pressure to the synthesis reaction column 1 through the line f to purge the cleavage cocktail remaining in the resin in the column, along with the above-described TFA or acetic acid, into the flask 3.

Next, nitrogen gas 7 is supplied to the flask 3 through lines a and b, followed by bubbling under cooling conditions (under 10° C. ). At this time valve 12 is closed to allow exhaust through line j. The peptide concentration in the cleavage cocktail can be increased by this procedure. In some cases, this procedure increases the peptide yield.

Step (9): Dry diethyl ether is added to the flask 3 from the funnel 2. Alternatively, diethyl ether is supplied from the funnel 4 to the flask 3 through the line d. Also, diethyl ether can be supplied to the flask 3 with a pump 13 or by application of increased pressure on the bottle of diethyl ether through the lines i and c. In these cases, nitrogen gas 8 or 9 is supplied to the flask 3 through the lines f, d and c or lines i and c, followed by stirring with bubbling. During this operation it is preferable to cool the flask 3 using the outside bath 6. Although the time required for this procedure is about 0.5 hours, the peptide yield may increase in some cases when the flask 3 is kept standing under cooling conditions overnight. As needed, when the desired peptide is aliphatic or not solidified by diethyl ether, petroleum ether or n-hexane can be used in combination with or in place of diethyl ether.

After the above procedure, the flask 3 is detached, and the precipitate therein is collected by filtration, which is then dried to yield the desired peptide in a crude form.

Step (10): The resulting crude peptide is purified by an appropriate conventional method.

In the above-described Steps (1) through (10), each valve operation, pressure control, reagent addition and other operations can be automated, for example, using a computer.

EXAMPLE

The present invention is hereinafter described in more detail by means of the following working example, but the present invention is not limited by it.
Example 1: Semi-preparative synthesis of Neurokinin A The desired peptide, His-Lys-Thr-Asp-Ser-Phe-Val-Gly-Leu-Met-NH$_2$ (SEQ ID NO: 1), is synthesized by an ordinary continuous flow synthesis using the following resin:
Resin: Tentagel SRAM™ (manufactured by Rapp Polymer Germany)
Resin substitution: 0.21 meq/g, 20 g.

To remove NαFmoc group, piperidine (20% in DMF) is used. The following amino acid derivatives are used in 4-fold excess:

| | |
|---|---|
| Fmoc-Met-OH | 6.24 g |
| Fmoc-Leu-OH | 5.94 g |
| Fmoc-Gly-OH | 4.99 g |
| Fmoc-Val-OH | 5.70 g |
| Fmoc-Phe-OH | 6.51 g |
| Fmoc-Ser(tBu)-OH | 6.44 g |
| Fmoc-Asp(OtBu)-OH | 6.91 g |
| Fmoc-Thr(tBu)-OH | 6.68 g |

-continued

| | |
|---|---|
| Fmoc-Lys(Boc)-OH | 7.87 g |
| Fmoc-His(Trt)-OH | 10.41 g |

Each coupling is carried out with reagents BOP(benzotriazol-1-yl-oxy-tris(dimethylamino) phosphonium hexafluorophosphate), HOBt(1-hydroxybenzotriazole) and NMM(N-methylmorpholine) in the presence of DMF as a reaction solvent. After the Nα Fmoc group is removed, the peptide is cleaved from the solid support and side chain protecting groups are simultaneously removed using the cleavage apparatus of the present invention shown in FIG. 1.

Specifically, the column used for peptide synthesis, as such, is first attached to the cleavage apparatus shown in FIG. 1 as the synthesis reaction column 1 (above-described Step (1)).

Next, methanol, t-butyl methyl ether and diethyl ether, as washing liquids, are supplied in this order from the funnel 2 to the flask 3 (eggplant-type flask) and then to the synthesis reaction column 1 to wash the peptidyl resin, instead of supplying them to the synthesis reaction column 1 through line i. After washing, the waste liquid is discarded through line e (above-described Step (2)).

Furthermore, to discard the ether remaining in the flask 3, the flask 3 is replaced with a new one before proceeding to the next step.

Next, nitrogen gas 7 is supplied under increased pressure through line a, passed through lines b, c and d, and then discharged through line e to dry the inside of the synthesis reaction column 1 (above-described Step(3)), after which a cleavage cocktail (a mixture of 94% TFA, 5% anisole and 1% ethanedithiol, 150 ml) is supplied from the funnel 4 to the flask 3. Nitrogen gas 7 is supplied under increased pressure through line a, and the cleavage cocktail in the flask 3 is transferred to the synthesis reaction column 1 through cleavage cocktail transport lines (lines c and d) to fill the synthesis reaction column 1 therewith (above-described Step (4)).

Nitrogen gas 8 is supplied under increased pressure to the synthesis reaction column 1 through line f, and the cleavage cocktail, which has entered the synthesis reaction column 1, is returned to the 1000-ml flask 3 through cleavage cocktail transport lines (lines d and c) (above-described Step (5)).

Next, the cleavage cocktail in the flask 3 is again injected to the synthesis reaction column 1 through cleavage cocktail transport lines (lines c and d) (above-described Step (6)). The procedures of the above-described Steps (5) and (6) are repeated for about 90 minutes at intervals of about 5 to 10 minutes to complete the cleavage of the desired peptide (above-described Step (7)).

After completion of cleavage, nitrogen gas 8 is supplied through line f to purge the cleavage cocktail into the flask 3 (above-described Step (8)). Nitrogen gas 7 is supplied to the flask 3 through lines a and b, and while bubbling, a part of the cleavage cocktail is removed to reduce its volume (above-described Step (9)). During this operation the flask 3 is cooled using the outside bath 6.

In this example, the above-described procedures are automatically performed using a computer.

Figure 2:
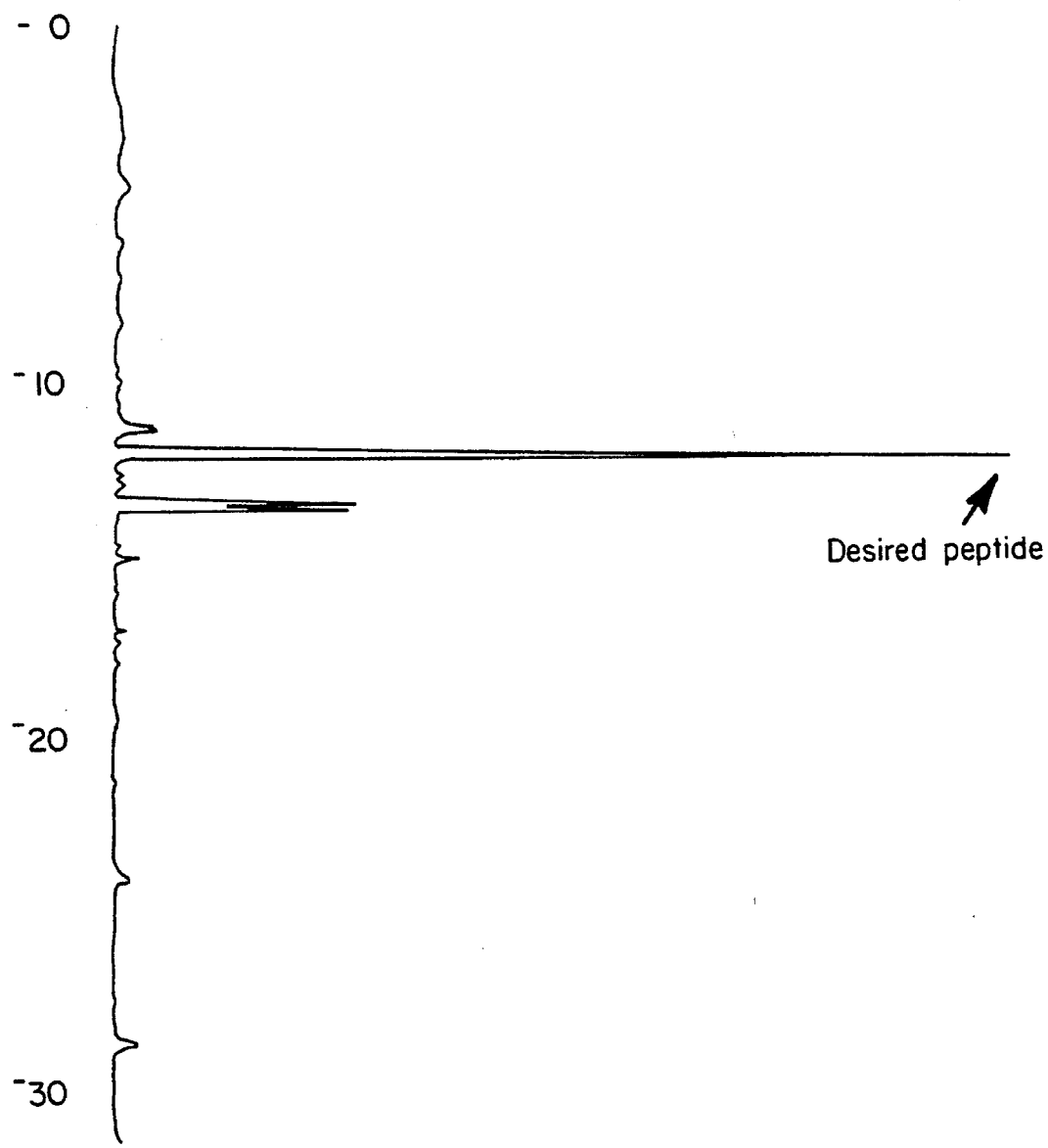
FIG. 2 shows a reverse HPLC trace of the crude peptide obtained with the cleavage apparatus of the present invention.

Next, 850 ml of dry diethyl ether are added from the funnel 2 to the flask 3, and the flask is kept standing under cooling conditions for 3 hours. Then, the flask 3, in which the peptide precipitates, is detached, and the precipitate is collected by filtration and dried to yield 5 g of the desired peptide in a crude form. The crude peptide is subject to sequence analysis to confirm the desired amino acid sequence. In addition, FAB-MS using Kratos MS50 reveals a mass number $[M+H]^+$ of 1134.5. Reverse phase HPLC trace of this crude peptide is shown in FIG. 2.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cleavage apparatus for cleaving a peptide-solid support bond and removing side chain protecting groups to liberate a peptide assembled on said solid support by solid-phase peptide synthesis, comprising:

a column for cleavage in which said peptide assembled on said solid support is present;

a cleavage cocktail supply bottle in which cleavage cocktail is contained, wherein said cleavage cocktail is a mixture of one or more reagents which liberates said peptide from said solid support;

a cleavage cocktail transport line connecting said column for cleavage and said cleavage cocktail supply bottle, through which said cleavage cocktail is supplied from said cleavage cocktail supply bottle to said column for cleavage and recovered into said cleavage cocktail supply bottle from said column for cleavage; and gas supply means by which said cleavage cocktail is transported in said cleavage cocktail transport line, said gas supply means comprising a first gas supply means and a second gas supply means, said first gas supply means being connected to said cleavage cocktail supply bottle, and said second gas supply means being connected to said column for cleavage.

2. The cleavage apparatus according to claim 1, further comprising a washing means to wash said peptide assembled on said solid support in said column for cleavage, said washing means being connected to said column for cleavage.

3. The cleavage apparatus according to claim 1, further comprising a means for controlling temperature in said cleavage cocktail supply bottle to keep said cleavage cocktail at a suitable temperature for cleavage.

4. The cleavage apparatus according to claim 3, wherein said means for controlling temperature in said cleavage cocktail supply bottle is an outside bath.

5. The cleavage apparatus according to claim 1, wherein said column for cleavage is a peptide synthesis column.

6. The cleavage apparatus according to claim 1, wherein said one or more reagents suitable for liberating said peptide from said solid support is selected from the group consisting of trifluoroacetic acid, anisole, thioanisole, ethanedithiol, dimethyl sulfide, ethyl methyl sulfide, phenol, and thiophenol.

7. A cleavage apparatus for cleaving a peptide-solid support bond and removing side chain protecting groups to liberate a peptide assembled on said solid support by solid-phase peptide synthesis, comprising:

a peptide synthesis column in which said peptide assembled on said solid support is present;

a washing means to wash said peptide assembled on said solid support in said peptide synthesis column, said washing means being connected to said peptide synthesis column;

a cleavage cocktail supply bottle in which cleavage cocktail is contained, wherein said cleavage cocktail is a mixture of one or more reagents which liberates said peptide from said solid support;

a means for controlling temperature in said cleavage cocktail supply bottle to keep said cleavage cocktail at a suitable temperature for cleavage;

a cleavage cocktail transport line connecting said peptide synthesis column and said cleavage cocktail supply bottle, through which said cleavage cocktail is supplied from said cleavage cocktail supply bottle to said peptide synthesis column and recovered into said cleavage cocktail supply bottle from said peptide synthesis column; and gas supply means by which said cleavage cocktail is transported in said cleavage cocktail transport line, said gas supply means comprising a first gas supply means and a second gas supply means, said first gas supply means being connected to said cleavage cocktail supply bottle, and said second gas supply means being connected to said peptide synthesis column.

8. The cleavage apparatus according to claim 7, wherein said means for controlling temperature in said cleavage cocktail supply bottle is an outside bath.

9. A method for cleaving a peptide-solid support bond and removing side chain protecting groups to liberate a peptide assembled on said solid support by solid-phase peptide synthesis, comprising:

providing a column for cleavage containing a peptide or a side chain protected peptide bound to said solid support after completion of peptide assembly, wherein said column for cleavage is connected to a cleavage cocktail supply bottle containing cleavage cocktail via a cleavage cocktail transport line through which said cleavage cocktail is supplied from said cleavage cocktail supply bottle to said column for cleavage and recovered into said cleavage cocktail supply bottle from said column for cleavage, and wherein a first gas supply means is connected to said cleavage cocktail supply bottle and a second gas supply means is connected to said column for cleavage, by which said cleavage cocktail is transported in said cleavage cocktail transport line;

cleaving said peptide-solid support bond and removing side chain protecting groups to liberate said peptide by circulating said cleavage cocktail between said cleavage cocktail supply bottle and said column for cleavage, wherein said circulating is carried out by supplying said cleavage cocktail to said column for cleavage from said cleavage cocktail supply bottle through said cleavage cocktail transport line by supplying gas under pressure to said cleavage cocktail supply bottle from said first gas supply means connected to said cleavage cocktail supply bottle, and returning said cleavage cocktail to said cleavage cocktail supply bottle through said cleavage cocktail transport line by supplying gas under pressure to said column for cleavage from said second gas supply means connected to said column for cleavage; and recovering said peptide from said cleavage cocktail supply bottle.

10. The method according to claim 9, further comprising washing said peptide assembled on said solid support in said column for cleavage via a washing means connected to said column for cleavage.

11. The method according to claim 9, further comprising controlling temperature in said cleavage cocktail supply bottle to keep said cleavage cocktail at a suitable temperature for cleavage.

12. The method according to claim 11, wherein said controlling said temperature in said cleavage cocktail supply bottle is performed using an outside bath.

13. The method according to claim 9, wherein said column for cleavage is a peptide synthesis column.

14. The method according to claim 9, wherein said one or more reagents suitable for liberating said peptide from said solid support is selected from the group consisting of trifluoroacetic acid, anisole, thioanisole, ethanedithiol, dimethyl sulfide, ethyl methyl sulfide, phenol, and thiophenol.

15. The method according to claim 9, wherein said circulating is repeated from about 9 to 18 cycles.

16. The method according to claim 15, wherein said circulating is repeated from about 9 to 18 cycles for about 90 minutes at intervals of about 5 to 10 minutes.

17. A method for cleaving a peptide-solid support bond and removing side chain protecting groups to liberate a peptide assembled on said solid support by solid-phase peptide synthesis, comprising:

providing a peptide synthesis column containing a peptide or a side chain protected peptide bound to said solid support after completion of peptide assembly, wherein said peptide synthesis column is connected to a cleavage cocktail supply bottle containing cleavage cocktail via a cleavage cocktail transport line through which said cleavage cocktail is supplied from said cleavage cocktail supply bottle to said peptide synthesis column and recovered into said cleavage cocktail supply bottle from said peptide synthesis column, and wherein a first gas supply means is connected to said cleavage cocktail supply bottle and a second gas supply means is connected to said peptide synthesis column, by which said cleavage cocktail is transported in said cleavage cocktail transport line;

washing said peptide assembled on said solid support in said peptide synthesis column via a washing means connected to said peptide synthesis column;

cleaving said peptide-solid support bond and removing side chain protecting groups to liberate said peptide by circulating said cleavage cocktail between said cleavage cocktail supply bottle and said peptide synthesis column, wherein said circulating is repeated from about 9 to 18 cycles for about 90 minutes at intervals of about 5 to 10 minutes by supplying said cleavage cocktail to said peptide synthesis column from said cleavage cocktail supply bottle through said cleavage cocktail transport line by supplying gas under pressure to said cleavage cocktail supply bottle from said first gas supply means connected to said cleavage cocktail supply bottle, and returning said cleavage cocktail to said cleavage cocktail supply bottle through said cleavage cocktail transport line by supplying gas under pressure to said peptide synthesis column from said second gas supply means connected to said peptide synthesis column, and wherein the temperature in said cleavage cocktail supply bottle is controlled to keep said cleavage cocktail at a suitable temperature for cleavage by using an outside bath; and recovering said peptide from said cleavage cocktail supply bottle.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( i x ) FEATURE:
( A ) NAME/KEY: Modified-site
( B ) LOCATION: 10
( D ) OTHER INFORMATION: /label=amidated
/ note="C-terminal methionine is amidated."

( x i ) SEQUENCE DESCRIPTION: SEQ ID NO:1:

His  Lys  Thr  Asp  Ser  Phe  Val  Gly  Leu  Met